United States Patent
Kobayashi et al.

(10) Patent No.: US 6,992,210 B2
(45) Date of Patent: Jan. 31, 2006

(54) FLUORINE-CONTAINING CYCLIC ESTERS, FLUORINE-CONTAINING CYCLIC ALCOHOLS, AND THEIR PRODUCTION PROCESSES

(75) Inventors: Satoru Kobayashi, Kawagoe (JP); Katsunori Kawamura, Kawagoe (JP); Haruhiko Komoriya, Kawagoe (JP); Kazuhiko Maeda, Chiyoda-ku (JP)

(73) Assignee: Central Glass Company, Limited, Ube (JP)

( * ) Notice: Subject to any disclaimer, the term of this patent is extended or adjusted under 35 U.S.C. 154(b) by 0 days.

(21) Appl. No.: 10/787,964

(22) Filed: Feb. 27, 2004

(65) Prior Publication Data

US 2004/0180954 A1 Sep. 16, 2004

(30) Foreign Application Priority Data

Mar. 11, 2003 (JP) ............................. 2003-064333

(51) Int. Cl.
*C07C 69/613* (2006.01)

(52) U.S. Cl. .................................... 560/227

(58) Field of Classification Search ............... 560/227
See application file for complete search history.

(56) References Cited

U.S. PATENT DOCUMENTS 6,414,167 B1 *  7/2002  Miyazawa et al. .......... 549/512

FOREIGN PATENT DOCUMENTS

JP          2002-80431          3/2002

* cited by examiner

*Primary Examiner*—Elvis O. Price
(74) *Attorney, Agent, or Firm*—Crowell & Moring LLP

(57) ABSTRACT

A fluorine-containing cyclic ester is represented by the formula 1:

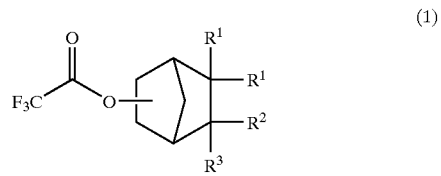

wherein each $R^1$ independently represents —H or —F, wherein $R^2$ is one selected from the group consisting of —H, —F, —$CF_3$, —OH, —COOH and —$COOR^4$, where $R^4$ is an alkyl group having a carbon atom number of 1–15, and wherein $R^3$ is a substituent selected from the group consisting of —F, —$CF_3$, and —$R^5C(CF_3)_2OR^6$, where $R^5$ is one selected from the group consisting of $CH_2$, $C_2H_4$, and $OCH_2$, and $R^6$ is H or an acid-labile protecting group.

11 Claims, No Drawings

FLUORINE-CONTAINING CYCLIC ESTERS, FLUORINE-CONTAINING CYCLIC ALCOHOLS, AND THEIR PRODUCTION PROCESSES

BACKGROUND OF THE INVENTION

The present invention relates to fluorine-containing cyclic esters and fluorine-containing cyclic alcohols, which are useful as raw materials for producing functional materials (e.g., polymers and resist compositions), medicines and agricultural chemicals, and their production processes.

Hitherto, fluorine-containing esters and fluorine-containing alcohols (derived from such esters) have been known as being useful as raw materials for producing various polymers, functional materials, medicines, and agricultural chemicals. In particular, fluorine-containing cyclic esters and fluorine-containing cyclic alcohols, which have cyclic structures in the molecules, are important precursors as raw materials for synthesizing monomers for functional materials.

U.S. Pat. No. 6,414,167 B1, corresponding to Japanese Patent Application Publication 2002-80431 A1, discloses octafluorotricyclodecane derivatives and processes for producing the same.

SUMMARY OF THE INVENTION

It is an object of the present invention to provide a novel fluorine-containing cyclic ester.

It is another object of the present invention to provide a process for producing the fluorine-containing cyclic ester.

According to the present invention, there is provided a fluorine-containing cyclic ester represented by the formula 1:

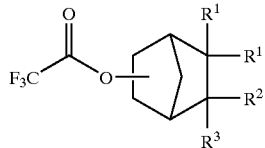

(1)

wherein each $R^1$ independently represents —H or —F,
wherein $R^2$ is one selected from the group consisting of —H, —F, —CF$_3$, —OH, —COOH and —COOR$^4$, where $R^4$ is an alkyl group having a carbon atom number of 1–15,
wherein $R^3$ is a substituent selected from the group consisting of —F, —CF$_3$, and —R$^5$C(CF$_3$)$_2$OR$^6$, where $R^5$ is one selected from the group consisting of CH$_2$, C$_2$H$_4$, and OCH$_2$, and $R^6$ is H or an acid-labile protecting group.

According to the present invention, there is provided a process for producing the fluorine-containing cyclic ester represented by the formula 1. The process comprises the step of reacting a fluorine-containing norbornene represented by the formula 5 with trifluoroacetic acid, thereby producing the fluorine-containing cyclic ester.

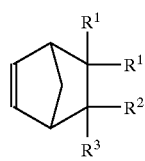

(5)

wherein $R^1$, $R^2$ and $R^3$ are defined as in the formula 1.

DESCRIPTION OF THE PREFERRED EMBODIMENTS

The above fluorine-containing cyclic ester (represented by the formula 1) of the present invention and the aftermentioned fluorine-containing cyclic alcohol of the present invention, which is derived from the fluorine-containing cyclic ester, are useful as raw materials for producing functional materials (e.g., polymers and resist compositions), medicines and agricultural chemicals.

Specific examples of the fluorine-containing cyclic ester represented by the formula 1 include those represented by the following formulas 6:

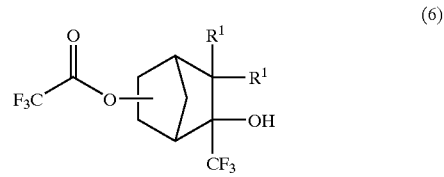

(6)

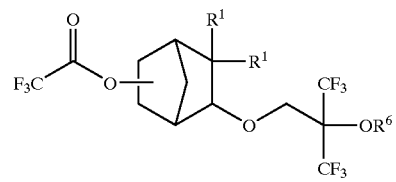

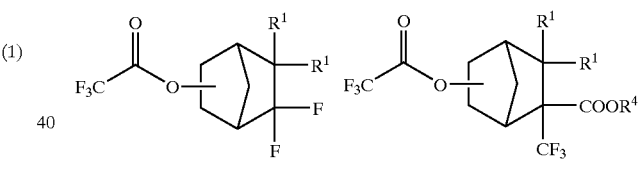

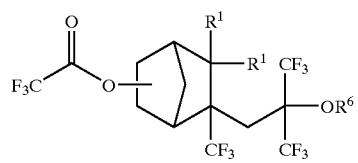

wherein $R^1$, $R^4$ and $R^6$ are defined as in the formula 1. Of the above examples, one containing a unit (—C(CF$_3$)$_2$—OR$^6$) derived from hexafluoroisopropanol is useful as a raw material monomer for producing functional materials such as resist compositions. As stated above, $R^6$ represents H or an acid-labile protecting group. This acid-labile protecting group may contain a hetero atom(s) such as oxygen. Examples of the acid-labile protecting group include tert-butoxycarbonyl group, methoxymethyl group, 2-methyl-2-adamantylester group, and 2-ethyl-2-adamantylester group.

In producing the fluorine-containing cyclic ester of the present invention, it is preferable to add a carboxylic acid to a double bond of a fluorine-containing norbornene represented by the above formula 5 due to the reaction easiness. Furthermore, the carboxylic acid is preferably an α-fluorinecontaining carboxylic acid (particularly preferably trifluoroacetic acid), since the resulting ester (containing fluorine atoms at its α-position) can easily be hydrolyzed into a corresponding alcohol.

The reaction for producing the fluorine-containing cyclic ester can be conducted in a solvent. This solvent is not particularly limited, as long as it does not interfere with the target reaction. Its examples include common organic solvents such as tetrahydrofuran, diethyl ether, dimethylformamide, toluene, xylene, and methylene chloride. The reaction temperature is not particularly limited. It is preferably from −80° C. to +200° C. in view of reactivity and handling easiness of peripheral devices, more preferably from −30° C. to +100° C. The reaction product (a crude ester) may be separated and purified by common procedures, such as concentration, extraction, distillation, recrystallization, filtration, and column chromatography. These procedures may be combined together.

From the fluorine-containing cyclic ester, it is possible to easily produce a fluorine-containing cyclic alcohol represented by the formula 4:

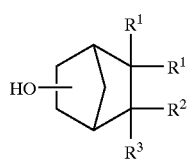
(4)

wherein $R^1$, $R^2$ and $R^3$ are defined as in the formula 1. This production can preferably be conducted by hydrolyzing the fluorine-containing cyclic ester, since the reaction (hydrolysis) occurs easily. This hydrolysis can be conducted by a known method without particular limitations with respect to the reaction conditions and reagents. It is possible to use a hydrolysis catalyst such as an inorganic base (e.g., sodium hydroxide and potassium hydroxide) or inorganic acid (e.g., hydrochloric acid and sulfuric acid).

The following nonlimitative examples are illustrative of the present invention.

EXAMPLE 1

Production of Fluorine-Containing Cyclic Ester 10 g of a fluorine-containing olefin represented by the following formula were dissolved in 20 mL of toluene in a 100 mL glass container. Then, 8.3 g of trifluoroacetic acid were gradually added, and stirring was conducted at room temperature for 5 hr. The obtained reaction solution was washed with water and saturated brine. The separated organic phase was dried with anhydrous magnesium sulfate, followed by distilling the solvent off under reduced pressure. After that, 11.4 g of a product were obtained by distillation. This product was identified by nuclear magnetic resonance spectrometry (NMR) and mass spectrometry as being a fluorine-containing cyclic ester represented by the following formula.

The identification data of the product were as follows.

$^{19}$F NMR (CDCl$_3$, CFCl$_3$ standard, 376 MHz) δ 75.8 (s), 75.9 (s), 76.0 (s), 76.4 (s), 77.1 (q, J=9.1), 77.4 (q, J=9.1), 77.8 (q, J=9.1), 78.0 (q, J=9.1). MS m/z (%) 388 (M$^+$, 1), 275(75), 247(35), 207(15), 107(100).

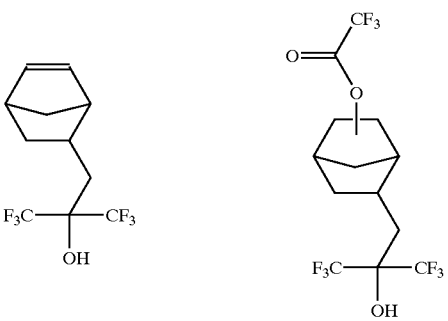

Fluorine-containing olefin    Fluorine-containing cyclic ester

EXAMPLE 2

Production of Fluorine-Coating Cyclic Alcohol

A 50 mL glass container was charged with 5 g of the fluorine-containing cyclic ester obtained by Example 1, 30 mL of water, 10 mL of methanol, and 1 g of sodium hydroxide, followed by stirring at room temperature for 2 hr. Then, pH of the resulting reaction mixture was adjusted to 2 by adding 10% hydrochloric acid aqueous solution, followed by extraction with toluene. The obtained organic layer was washed with water and saturated brine, followed by drying with anhydrous magnesium sulfate and then distilling the solvent off. After that, a product was obtained by distillation. This product was identified by NMR and mass spectrometry as being a fluorine-containing cyclic alcohol represented by the following formula.

The identification data of the product were as follows.

$^{19}$F NMR (CDCl$_3$, CFCl$_3$ standard, 376 MHz) δ 77.1 (q, J=9.1), 77.4 (q, J=9.1), 77.8 (q, J=9.1), 78.0 (q, J=9.1). MS m/z (%) 292(M$^+$, 1), 274(72), 246(43), 207(15), 107(100).

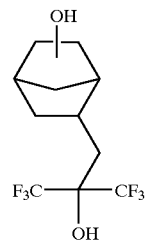

Fluorine-containing cyclic alcohol

The entire disclosure of Japanese Patent Application No. 2003-064333 (filed on Mar. 11, 2003), which is a basic Japanese patent application of the present application, including specification, claims and summary, is incorporated herein by reference in its entirety.

What is claimed is:

1. A fluorine-containing cyclic ester represented by the formula 1:

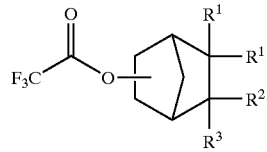

wherein each $R^1$ independently represents —H or —F, wherein $R^2$ is one selected from the group consisting of —H, —F, —CF$_3$, —OH, —COOH and —COOR$^4$, where $R^4$ is an alkyl group having a carbon atom number of 1–15, wherein $R^3$ is a substituent selected from the group consisting of —F, —CF$_3$, and —R$^5$C(CF$_3$)$_2$OR$^6$, where $R^5$ is one selected from the group consisting of CH$_2$, C$_2$H$_4$, and OCH$_2$, and $R^6$ is H or an acid-labile protecting group.

2. A fluorine-containing cyclic ester according to claim 1, wherein $R^3$ of the formula 1 is —R$^5$C(CF$_3$)$_2$OR$^6$, wherein $R^5$ and $R^6$ are defined as in formula 1.

3. A fluorine-containing cyclic ester according to claim 1, which is represented by the formula 3:

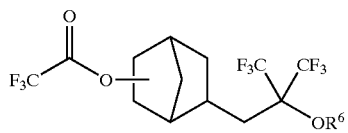

wherein $R^6$ is defined as in the formula 1.

4. A fluorine-containing cyclic ester according to claim 1, which is represented by one of the following formulas:

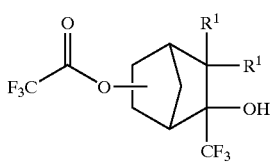

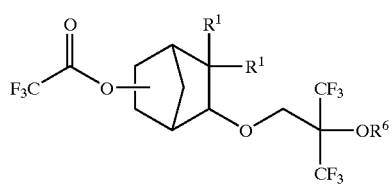

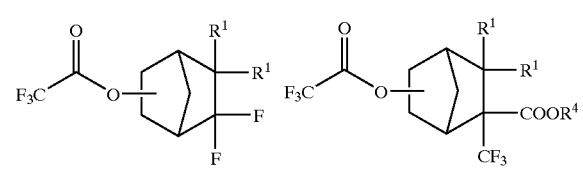

-continued

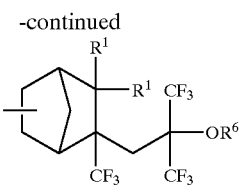

wherein $R^1$, $R^4$ and $R^6$ are defined as in the formula 1.

5. A fluorine-containing cyclic ester according to claim 1, wherein $R^6$ is an acid-labile protecting group selected from the group consisting of tert-butoxycarbonyl group, methoxymethyl group, 2-methyl-2-adamantylester group, and 2-ethyl-2-adamantylester group.

6. A process for producing a fluorine-containing cyclic ester represented by the formula 1, comprising the step of reacting a fluorine-containing norbornene represented by the formula 5 with trifluoroacetic acid,

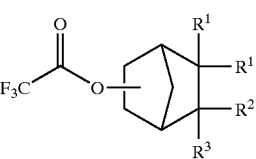

wherein each $R^1$ independently represents —H or —F, wherein $R^2$ is one selected from the group consisting of —H, —F, —CF$_3$, —OH, —COOH and —COOR$^4$, where $R^4$ is an alkyl group having a carbon atom number of 1–15, wherein $R^3$ is a substituent selected from the group consisting of —F, —CF$_3$, and —R$^5$C(CF$_3$)$_2$OR$^6$, where $R^5$ is one selected from the group consisting of CH$_2$, C$_2$H$_4$, and OCH$_2$, and $R^6$ is H or an acid-labile protecting group,

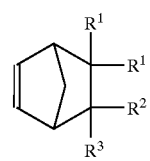

wherein $R^1$, $R^2$ and $R^3$ are defined as in the formula 1.

7. A process for producing a fluorine-containing cyclic alcohol represented by the formula 4, comprising the step of hydrolyzing a fluorine-containing cyclic ester represented by the formula 1 into the fluorine-containing cyclic alcohol,

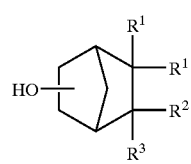

wherein each $R^1$ independently represents —H or —F, wherein $R^2$ is one selected from the group consisting of —H, —F, —CF$_3$, —OH, —COOH and —COOR$^4$, where $R^4$ is an alkyl group having a carbon atom number of 1–15, wherein $R^3$ is a substituent selected from the group consisting of —F, —$CF_3$, and —$R^5C(CF_3)_2OR^6$, where $R^5$ is one selected from the group consisting of $CH_2$, $C_2H_4$, and $OCH_2$, and $R^6$ is H or an acid-labile protecting group,

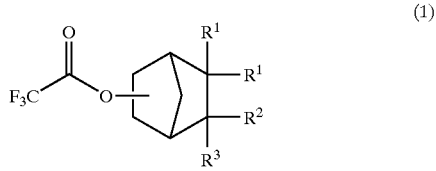

(1)

wherein $R^1$, $R^2$, and $R^3$ are defined as in the formula 4.

8. A process for producing a fluorine-containing cyclic alcohol represented by the formula 4, comprising the steps of:
(a) reacting a fluorine-containing norbornene represented by the formula 5 with trifluoroacetic acid to prepare a fluorine-containing cyclic ester represented by the formula 1; and
(b) hydrolyzing the fluorine-containing cyclic ester into the fluorine-containing cyclic alcohol,

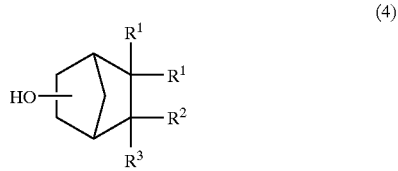

(4)

wherein each $R^1$ independently represents —H or —F,
wherein $R^2$ is one selected from the group consisting of —H, —F, —$CF_3$, —OH, —COOH and —$COOR^4$, where $R^4$ is an alkyl group having a carbon atom number of 1–15,
wherein $R^3$ is a substituent selected from the group consisting of —F, —$CF_3$, and —$R^5C(CF_3)_2OR^6$, where $R^5$ is one selected from the group consisting of $CH_2$, $C_2H_4$, and $OCH_2$, and $R^6$ is H or an acid-labile protecting group,

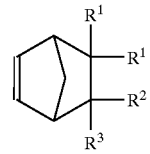

(5)

wherein $R^1$, $R^2$ and $R^3$ are defined as in the formula 4,

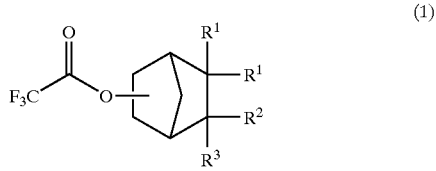

(1)

wherein $R^1$, $R^2$, and $R^3$ are defined as in the formula 4.

9. A process according to claim 6, wherein $R^6$ is an acid-labile protecting group selected from the group consisting of tert-butoxycarbonyl group, methoxymethyl group, 2-methyl-2-adamantylester group, and 2-ethyl-2-adamantylester group.

10. A process according to claim 7, wherein $R^6$ is an acid-labile protecting group selected from the group consisting of tert-butoxycarbonyl group, methoxymethyl group, 2-methyl-2-adamantylester group, and 2-ethyl-2-adamantylester group.

11. A process according to claim 8, wherein $R^6$ is an acid-labile protecting group selected from the group consisting of tert-butoxycarbonyl group, methoxymethyl group, 2-methyl-2-adamantylester group, and 2-ethyl-2-adamantylester group.

* * * * *